| United States Patent [19] | [11] Patent Number: 4,709,035 |
|---|---|
| Hartman | [45] Date of Patent: Nov. 24, 1987 |

[54] 2,6-DISUBSTITUTED DERIVATIVES OF 3-NITROPYRAZINES AS ADJUNCTS TO RADIATION THERAPY

[75] Inventor: George D. Hartman, Lansdale, Pa.

[73] Assignee: Merck & Co., Inc., Rahway, N.J.

[21] Appl. No.: 646,729

[22] Filed: Sep. 4, 1984

Related U.S. Application Data

[62] Division of Ser. No. 441,203, Nov. 12, 1982, abandoned.

[51] Int. Cl.[4] .................. A61K 31/495; C07D 241/16; C07D 241/24
[52] U.S. Cl. .................................... 544/407; 544/427; 544/408; 544/409; 514/255
[58] Field of Search ............... 544/407, 409, 408, 336; 514/255

[56] References Cited

U.S. PATENT DOCUMENTS 3,541,093  11/1970  Tull et al. ............................ 544/350
3,660,397  5/1972  Jones et al. ......................... 544/350
4,594,349  6/1986  Beyer .................................. 544/407

FOREIGN PATENT DOCUMENTS 1232758  5/1971  United Kingdom ................ 544/350

OTHER PUBLICATIONS

Hartman, et al., Non-Mutagenic Nitro-Heterocycles . . . ", Mutation Research 117(1983) 272–277.
Taylor, et al., Conversion of a Primary Amino Group into a Nitroso Group . . . ", J. Org. Chem. (1982) 47: 552–555.

*Primary Examiner*—Donald G. Daus
*Assistant Examiner*—G. Hendricks
*Attorney, Agent, or Firm*—Hesna J. Pfeiffer

[57] ABSTRACT

2,6-Disubstituted derivatives of 3-nitropyrazine are disclosed to have activity in increasing the sensitivity of tumor cells to radiation. Also disclosed are methods of preparing such compounds and pharmaceutical compositions including such compounds.

6 Claims, No Drawings

2,6-DISUBSTITUTED DERIVATIVES OF 3-NITROPYRAZINES USEFUL AS ADJUNCTS TO RADIATION THERAPY

This is a division of application Ser. No. 441,203, filed Nov. 12, 1982, now abandoned.

BACKGROUND OF THE INVENTION

This invention relates to 2 and/or 6 substituted 3-nitropyrazine compounds used as sensitizers of tumor cells to therapeutic radiation. It also relates to the process of preparing such compounds starting with chloroaminopyrazines, converting said chloroaminopyrazines to the corresponding chloronitropyrazines and aminating said chloronitropyrazines to produce the substituted nitropyrazines useful in tne sensitization of tumor cells to the therapeutic effect of radiation.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, but are believed to have a more favorable therapeutic ratio.

DETAILED DESCRIPTION OF THE INVENTION

The compositions of the present invention are nitropyrazine compounds of the formula

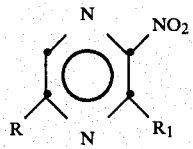

I wherein R and $R_1$ are each selected from the group consisting of
(a) hydrogen;
(b) carboalkoxy in which the alkoxy group contains from 1—3 carbon atoms;
(c)

wherein $R_2$ and $R_3$ are each selected from the group consisting of hydrogen and lower alkyl substituents of from 1 to 6 carbon atoms, said alkyl substituent having from 1-4 of the alkyl carbons substituted with a hydroxy or methoxy substituent;
provided that at least one of the R and $R_1$ substituents is a substituent other than hydrogen.

The compositions of the present invention that are particularly useful as radiation sensitizers are nitropyrazine compounds of the formula

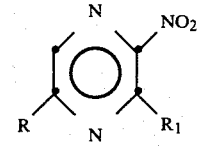

II wherein R and $R_1$ are each selected from the group consisting of
(a) hydrogen;
(b) carboalkoxy in which the alkoxy group contains from 1-3 carbon atoms;
(c)

wherein $R_2$ and $R_3$ are each selected from the group consisting of hydrogen and lower alkyl substituents of from 1 to 6 carbon atoms, said alkyl substituent having from 1-4 of the alkyl carbons substituted with a hydroxy substituent;
provided that at least one of the R and $R_1$ substituents is a substituent other than hydrogen.

The substituted nitropyrazine compounds of the present invention are prepared in the following manner:

A substituted aminopyrazine of the formula

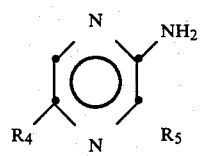

III wherein $R_4$ and $R_5$ are each selected from the group consisting of hydrogen, halogen and carboalkoxy substituents provided that at least one of $R_4$ and $R_5$ is a halogen, is treated with dimethyl sulfoxide and trifluoromethane sulfonic anhydride to produce a sulfilimine compound of the formula

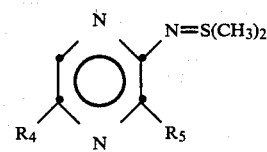

IV which is then oxidized to produce the corresponding nitropyrazine of the formula

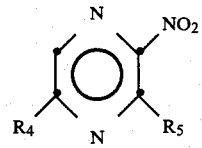

V

In carrying out the first step of the conversion the selected amino pyrazine of formula III, the reagent is prepared by mixing dimethylsulfoxide in methylene chloride and cooled to $-78°$ C. To the cooled solution is added trifluoromethane sulfonic anhydride in a ratio of approximately 3 moles dimethylsulfoxide to 2 moles of anhydride to produce dimethyl sulfide ditriflate of the formula

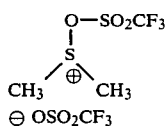

VI

Then, there is added to the cooled solution of VI the selected amino pyrazine of formula III while maintaining the temperature of the reaction mixture at −78° C. to produce the sulfilimine of formula IV. The resulting suspension is made alkaline with aqueous sodium bicarbonate or sodium hydroxide. Additional methylene chloride is added and the product extracted into the methylene chloride phase which is separated and evaporated to remove the volatile organic solvent leaving the sulfilimine IV as a residue.

The product is then oxidized while maintaining the temperature at or below 0° C. preferably using an organic peroxy carboxylic acid e.g., m-chloroperbenzoic acid as the oxidizing agent to produce the desired nitropyrazine of formula V.

Preferably, compounds of formula V wherein $R_4$ or $R_5$ is halogen are then treated with ammonia or an hydroxyalkylamine or an alkoxyalkylamine of the formula

wherein $R_2$ and $R_3$ are as defined hereinabove to produce a nitropyrazine of the formula

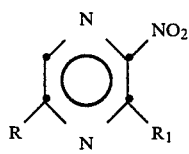

wherein at least one of R and $R_1$ is $NR_2R_3$ as defined hereinabove and the other of R and $R_1$ is defined as hydrogen or carboalkoxy in which the alkoxy group contains from 1-3 carbons.

The method of treatment of human patients or domestic animals undergoing radiation treatment of malignant disease processes employs the compounds of the present invention in pharmaceutical compositions that are administered orally or parenterally, or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface approximately equivalent to a dosage of 6 to 100 mg/kg of patient body weight as set forth in the "Nelson Textbook of Pediatrics" Eleventh Edition (1979) p. 31, edited by Vaughan, McKay, Behrman, and Nelson.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each suceeding radiation treatment, observing the patient carefully for any drug side effect. The composition to be administered is an effective amount of the active compound and a pharmaceutical carrier for said active compound. The dosage form for intravenous administration is a sterile isotonic solution of the drug. Oral dosage forms such as tablets, capsules, or elixirs are preferred.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention. Temperature are in degrees celsius unless otherwise indicated throughout the application.

EXAMPLE 1

3-Chloro-2-nitropyrazine

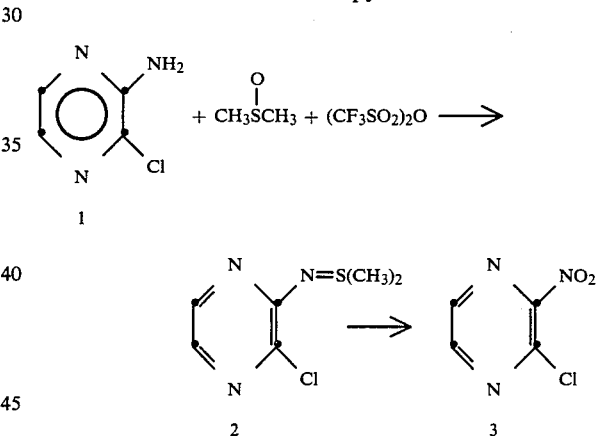

Step A: S,S-Dimethyl-N-(3-chloropyrazin-2-yl)sulfilimine (2)

To a mechanically stirred solution of 3.9 g (0.05 mol) dimethyl sulfoxide in 30 ml dry methylene chloride at −78° under nitrogen is added 13.1 g (0.046 mol) trifluoromethanesulfonic anhydride dropwise to afford a white precipitate. To this is added a solution of 5.0 g (0.039 mol) 2-amino-3-chloropyrazine (1) in 30 ml methylene chloride/15 ml dimethyl sulfoxide and the resulting solution is stirred at −78° for 2 hours and at −55° for 1 hour. The reaction mixture is then quenched with 50 ml of 5% aqueous sodium bicarbonate solution and stirred at −5° for 5 minutes. The reaction mixture is diluted with 200 ml methylene chloride and the phases are separated. The aqueous phase is extracted with 250 ml methylene chloride and the combined organic phases are washed with 3×75 ml portions of water and dried over anhydrous sodium sulfate. The solvent is removed from the rotary evaporator to give 5.8 g (79%) of 2 as yellow crystals, m.p. 106°-108°.

Step B: 3-Chloro-2-nitropyrazine (3)

To 7.9 g (0.46 mol, 80–90%) m-chloroperbenzoic acid in 70 ml methylene chloride cooled to −5° and stirred mechanically is added a solution of 5.36 g (0.028 mol) 2 in 30 ml methylene chloride dropwise at such a rate that the temperature does not exceed 0°. The reaction mixture is stirred at 0° for 40 minutes and then 3 ml of dimethyl sulfide is added with stirring for another 10 minutes at 0°. The cold reaction mixture is filtered quickly to afford a clear, green solution of the nitroso derivative. This solution is cooled to 0° and ozone is bubbled through until the solution is nearly colorless. The resulting suspension is extracted with 2×50 ml saturated sodium bicarbonate and the organic phase is dried over anhydrous sodium sulfate. The solvent is removed from the rotary evaporator to give a yellow oil which is purified by flash chromatography on silica gel with chloroform elution. Pure 3 is a pungent, yellow oil.

EXAMPLE 2

2-Chloro-5-nitropyrazine

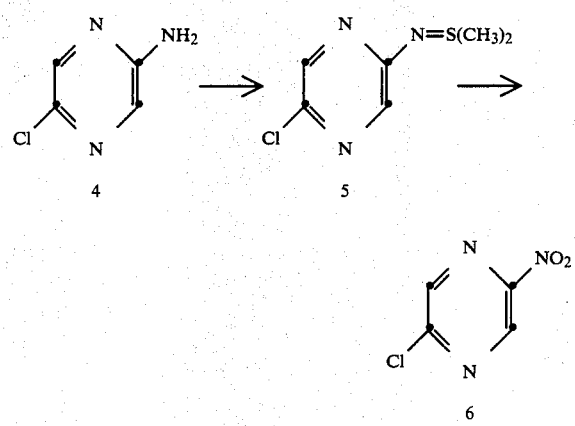

Step A: S,S-Deimethyl-N-(5-chloropyrazin-2-yl)sulfilimine (5)

Compound 5 is prepared from 2-amino-5-chloropyrazine as described above for 2 in Example 1A to afford pure 5 as a smelly, tan solid, m.p. 119°–120°.

Step B: 2-Chloro-5-nitropyrazine (6)

Compound 6 is prepared as described in Example 1B for 3, to afford pure 6 as yellow crystals, m.p. 90–92.

EXAMPLE 3

Methyl-6-chloro-3-nitropyrazinoate 9

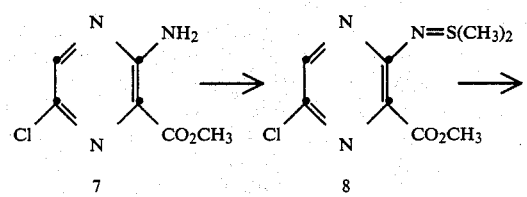

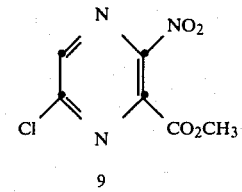

Step A: S,S-Dimethyl-N-(5-chloro-3-methoxycarbonylpyrazin-2-yl)sulfilimine (8)

Compound 8 is prepared from methyl 6-chloro-3-aminopyrazinoate (7) as described in Example 1A for 2, to afford crude 8 which is recrystallized from methylene chloride/hexane. Pure 8 is obtained as a yellow solid, m.p. 167°–9°.

Step B: Methyl 6-chloro-3-nitropyrazinoate (9)

Compound 9 is prepared from 8 as described in Example 1B for 3, to give crude 9 which is purified by flash chromatography on silica gel eluting with 2% methanol/chloroform. Pure 9 s a pungent yellow oil.

EXAMPLE 4

2-(2,3-Dihydroxypropyl)amino-3-nitropyrazine

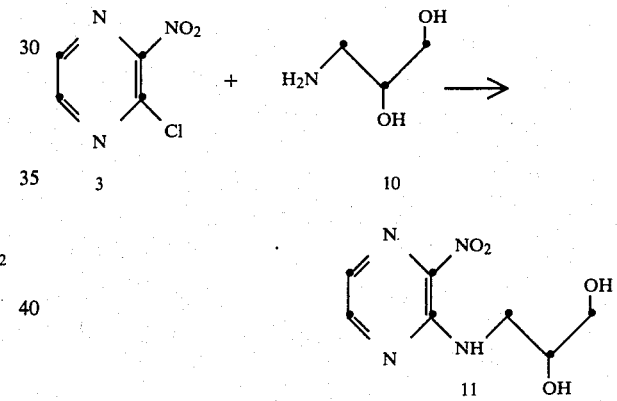

2-(2,3-Dihydroxypropyl)amino-3-nitropyrazine (11)

To a solution of 1.5 g (0.0094 mol) 3 and 1.01 g (0.01 mol) triethylamine in 25 ml isopropanol is added 0.91 g (0.01 mol) 3-amino-1,2-propanediol (10). The reaction mixture becomes reddish and is stirred at room temperature for 16 hours. The solvent is then removed on the rotary evaporator and the residue is purified by flash chromatography on silica gel to afford pure 11 as a yellow solid, m.p. 100°–102°.

EXAMPLE 5

2-(2,3-Dihydroxypropyl)amino-5-nitropyrazine

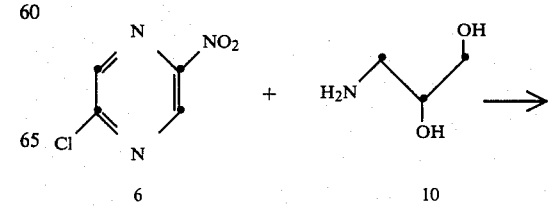

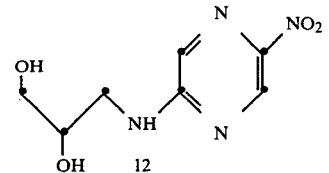

2-(2,3-Dihydroxypropyl)amino-5-nitropyrazine (12)

To a solution of 0.5 g (0.003 mol) 6 and 0.3 g (0.003 mol) triethylamine in 10 ml acetonitrile is added 0.32 g (0.0035 mol) 3-amino-1,2-propanediol (10) in 10 ml isopropanol. After stirring for 18 hours at room temperature the solvent is removed on the rotary evaporator and the residue is purified by flash chromatography on silica gel eluting with 10% methanol/chloroform. Pure 12 has Rf 0.4 and is a pale yellow solid, m.p. 185°–7°.

EXAMPLE 6

3-(5-Nitropyrazin-2-yl)amino-1,2,4-butanetriol

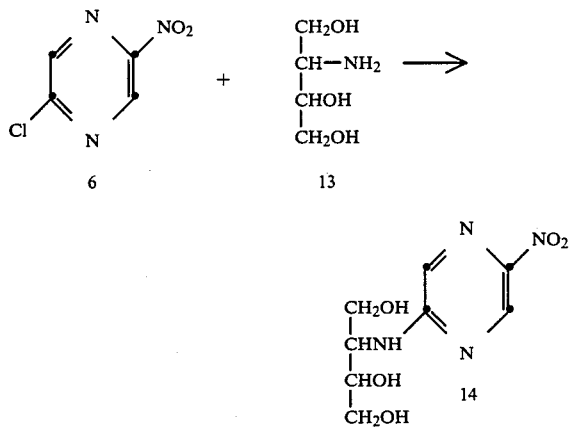

3-(5-Nitropyrazin-2-yl)amino-1,2,4-butanetriol (14)

To 0.5 g (0.003 mol) 6 dissolved in 15 ml acetonitrile is added a solution of 0.3 g (0.003 mol) triethylamine and 0.36 g (0.003 mol) 3-amino-1,2,4-butanetriol in 15 ml isopropanol. The reaction mixture becomes reddish in color and is stirred for 16 hours at room temperature. The solvent is removed from the rotary evaporator and the residue is purified by flash chromatography on silica gel eluting with 20% methanol/chloroform. Pure 14 has Rf 0.4 and is obtained as a pale, yellow solid, m.p. 133°–5°.

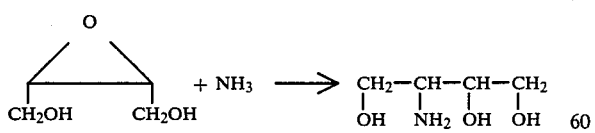

A pressure reactor is charged with 10.0g of 1,4-butane-2,3-epoxide, 30 ml liquid ammonia and 100 ml EtOH. The reaction vessel is sealed and heated at 100° for 10 hrs.

The reaction mixture is then stripped on the rotary evaporator to leave a clear, oil which is triturated with ether to afford the desired product as a viscous oil.

EXAMPLE 7

Methyl 6-(2,3-dihydroxypropyl)amino-3-nitropyrazinoate

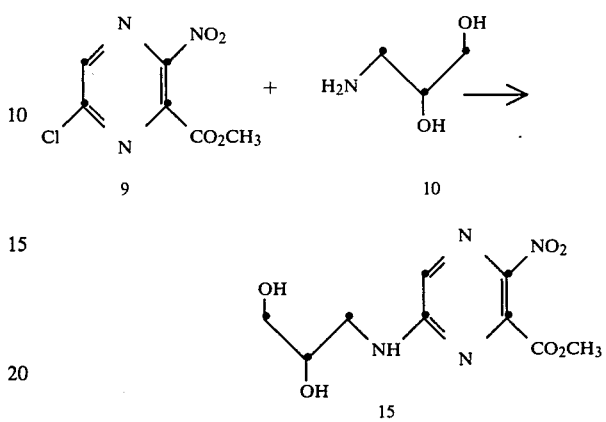

Methyl 6-(2,3-dihydroxypropyl)amino-3-nitropyrazinoate (15)

To 1.0 g (0.004 mol) 9 in 15 ml isopropanol is added 0.36 g (0.004 mol) 10 and 0.4 g (0.004 mol) triethylamine at room temperature. The reaction mixture becomes reddish in color and is stirred at room temperature for 16 hours. The solvent is removed on the rotary evaporator and the residue is purified by flash chromatography on silica gel followed by elution with 10% methanol/chloroform. Pure 15 has Rf 0.4 and is obtained as a yellow solid, m.p 107°–9°.

What is claimed is:

1. A nitropyrazine compound of the formula

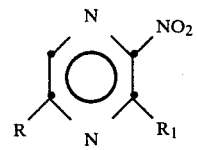

wherein R and $R_1$ are each selected from the group consisting of
   (a) hydrogen;
   (b) carboalkoxy in which the alkoxy group has from 1–3 carbon atoms;
   (c)

wherein $R_2$ and $R_3$ are each selected from the group consisting of hydrogen and lower alkyl substituents of from 1 to 6 carbon atoms, said alkyl substituent having from 1–4 of the alkyl carbons substituted with a hydroxy or methoxy substituent; provided tnat at least one of the R and $R_1$ substituents is a substituent other than hydrogen.

2. A nitropyrazine compound according to Claim 1 wherein R and $R_1$ are each selected from the group consisting of
   (a) hydrogen;

(b) carboalkoxy in which the alkoxy group has from 1–3 carbon atoms;
(c)

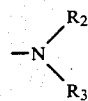

wherein $R_2$ and $R_3$ are each selected from the group consisting of hydrogen and lower alkyl substituents of from 1 to 6 carbon atoms, said alkyl substituent having from 1–4 of the alkyl carbons substituted with a hydroxy substituent;

provided that at least one of the R and $R_1$ substituents is a substituent other than hydrogen.

3. A compound according to claim 2 which is 2-(2,3-dihydroxypropyl)amino-3-nitropyrazine.

4. A compound according to claim 2 which is 2-(2,3-dihydroxypropyl)amino-5-nitropyrazine.

5. A compound according to claim 2 which is 3-(5-nitropyrazine-2-yl)amino-1,2,4-butanetriol.

6. A compound according to claim 2 which is methyl 6-(2,3-dihydroxypropyl)amino-3-nitropyrazinoate.

* * * * *